US009566355B2

(12) United States Patent  
Matosziuk et al.

(10) Patent No.: US 9,566,355 B2  
(45) Date of Patent: Feb. 14, 2017

(54) BACTERIA-TARGETED MAGNETIC RESONANCE CONTRAST AGENTS

(71) Applicant: Northwestern University, Evanston, IL (US)

(72) Inventors: Lauren M. Matosziuk, Evanston, IL (US); Allison S. Harney, Bronx, NY (US); Keith W. MacRenaris, Evanston, IL (US); Thomas J. Meade, Wilmette, IL (US)

(73) Assignee: Northwestern University, Evanston, IL (US)

( * ) Notice: Subject to any disclaimer, the term of this patent is extended or adjusted under 35 U.S.C. 154(b) by 142 days.

(21) Appl. No.: 14/198,853

(22) Filed: Mar. 6, 2014

(65) Prior Publication Data

US 2014/0271490 A1     Sep. 18, 2014

Related U.S. Application Data

(60) Provisional application No. 61/779,115, filed on Mar. 13, 2013.

(51) Int. Cl.
    *A61K 49/00*      (2006.01)
    *A61K 49/08*      (2006.01)
    *C07F 5/00*      (2006.01)
    *C12Q 1/10*      (2006.01)
    *C12Q 1/14*      (2006.01)
    *A61K 49/10*      (2006.01)

(52) U.S. Cl.
    CPC ........... *A61K 49/085* (2013.01); *A61K 49/106* (2013.01); *C07F 5/003* (2013.01); *C12Q 1/10* (2013.01); *C12Q 1/14* (2013.01)

(58) Field of Classification Search
    CPC .... A61K 49/00; A61K 49/085; A61K 49/106; C07F 5/003; C12Q 1/10; C12Q 1/14
    USPC ... 424/1.11, 1.65, 9.1, 9.2, 9.3, 9.4, 9.5, 9.6; 534/7, 10–16; 530/300; 514/1, 1.1
    See application file for complete search history.

(56) References Cited

U.S. PATENT DOCUMENTS 9,012,242 B2 * 4/2015 Singh ................. A61K 49/0032
                                                              436/546

OTHER PUBLICATIONS

Liu et al, Nuclear Medicine and Biology, Feb. 10, 2012, vol. 39, pp. 709-714.*
Omar, Journal of Thermal Analysis and Calorimetry, 2009, vol. 96, No. 2, pp. 607-615.*
Ojida et al, Bull. Chem. Soc., Jpn., 2006, vol. 79, No. 1, pp. 35-46.*
Lakshmi et al, Tetrahedron, 2004, vol. 60, pp. 11307-11315.*
Aime et al., "Dependence of the relaxivity and luminescence of gadolinium and europium amino-acid complexes on hydrogencarbonate and pH," Chem Commun, 1999, 1047-1048.
Alauddin et al., "Receptor mediated uptake of a radiolabeled contrast agent sensitive to beta-galactosidase activity," Nucl Med Biol, 2003, 30(3):261-265.
Allen et al., "Magnetic resonance contrast agents for medical and molecular imaging," Met Ions Biol Syst., 2004, 42:1-38.
Ashton et al., "The Synthesis and Characterization of a New Family of Polyamide Dendrimers," Chem Eur J, 1998, 4:781-795.
Aydinuraz et al., "In vitro *S. epidermidis* and *S. aureus* adherence to composite and lightweight polypropylene grafts," J Surg Res, 2009, 157(1):e79-e86.
Brouwer et al., "The use of technetium-99m radiolabeled human antimicrobial peptides for infection specific imaging," Mini Rev Med Chem, 2008, 8(10):1039-1052.
Caly et al., "A prospective study of bacterial infections in patients with cirrhosis," J Hepatol, 1993, 18(3):353-358.
Caravan, "Strategies for increasing the sensitivity of gadolinium based MRI contrast agents," Chem Soc Rev., 2006, 35(6):512-523.
Chew et al, "Ureteral stent symptoms and associated infections: a biomaterials perspective," Nat Rev Urol, 2009, 6(8):440-448.
Cilliers et al., "Modification of embolic-PVA particles with MR contrast agents," Magn Reson Med., 2008, 59(4):898-902.
De Luca et al., "An efficient route to alkyl chlorides from alcohols using the complex TCT/DMF," Org Lett, 2002, 4(4):553-555.
Divittorio et al., "Zinc(II) coordination complexes as membrane-active fluorescent probes and antibiotics," Chembiochem, 2008, 9(2):286-293.
Duimstra et al., "A gadolinium chelate for detection of beta-glucuronidase: a self-immolative approach," J Am Chem Soc., 2005, 127(37):12847-12855.
Ferrara et al., "Lipid-shelled vehicles: engineering for ultrasound molecular imaging and drug delivery," Acc Chem Res., 2009, 42(7):881-892.
Hall et al., "Relaxometric and luminescence behaviour of triaquahexaazamacrocyclic complexes, the gadolinium complex displaying a high relaxivity with a pronounced pH dependence," New J Chem., 1998, 22:627-631.
Harney et al., "Molecular imaging of in vivo gene expression," Future Med Chem., 2010, 2(3):503-519.
Hermann et al., "Gadolinium(III) complexes as MRI contrast agents: ligand design and properties of the complexes," Dalton Trans., 2008, (23):3027-3047.
Hirsch et al., "Impact of multidrug-resistant Pseudomonas aeruginosa infection on patient outcomes," Expert Rev Pharmaceocon Outcomes Res., 2010, 10(4):441-451.
Jaffer et al., "Molecular imaging in the clinical arena," JAMA, 2005, 293(7):855-862.
Koga, "Early evolution of membrane lipids: how did the lipid divide occur?," J Mol Evol, 2011, 72(3):274-282.
Kollef et al., "Inadequate antimicrobial treatment of infections: a risk factor for hospital mortality among critically ill patients," Chest, 1999, 115(2):462-474.

(Continued)

*Primary Examiner* — D L Jones
(74) *Attorney, Agent, or Firm* — Casimir Jones, S.C.; Jason Bond (57) ABSTRACT

The present invention relates to bacteria-targeted contrast agents for magnetic resonance imaging (MRI). In particular, the present invention relates to bacteria targeted MRI contrast agents that can be used to detect bacteria in vivo or in vitro. In certain embodiments, the contrast agents comprise a metal chelate conjugated to at least two Zn-dipicolylamine groups.

4 Claims, 6 Drawing Sheets

(56) References Cited

OTHER PUBLICATIONS

Lakshmi et al., "Fluorophore-linked zinc(II)dipicolylamine coordination complexes as sensors for phosphatidylserine-containing membranes," Tetrahedron, 2004, 60(49):11307-11315.
Lee et al., "Activatable imaging probes with amplified fluorescent signals," Chem Commun., 2008, (36):4250-4260.
Leevy et al., "Noninvasive optical imaging of *Staphylococcus aureus* bacterial infection in living mice using a Bis-dipicolylamine-Zinc(II) affinity group conjugated to a near-infrared fluorophore," Bioconjug Chem., 2008, 19(3):686-692.
Leevy et al., "Optical imaging of bacterial infection in living mice using a fluorescent near-infrared molecular probe," J Am Chem Soc., 2006, 128(51):16476-16477.
Leevy et al., "Selective recognition of bacterial membranes by zinc(II)-coordination complexes," Chem Commun (Camb), 2006, (15):1595-1597.
Li et al., "A Calcium-Sensitive Magnetic Resonance Imaging Contrast Agent," J Am Chem Soc., 1999, 121:1413-1414.
Li et al., "Mechanistic studies of a calcium-dependent MRI contrast agent," Inorg Chem., 2002, 41(15):4018-4024.
Linder, "Contrast ultrasound molecular imaging: harnessing the power of bubbles," Cardiovasc Res., 2009, 83(4):615-616.
Louie et al., "In vivo visualization of gene expression using magnetic resonance imaging," Nat Biotechnol., 2000, 18(3):321-3258.
Lowe et al., "pH-dependent modulation of relaxivity and luminescence in macrocyclic gadolinium and europium complexes based on reversible intramolecular sulfonamide ligation," J Am Chem Soc., 2001, 123(31):7601-7609.
Major et al., "Bioresponsive, cell-penetrating, and multimeric MR contrast agents," Acc Chem Res., 2009, 42(7):893-903.
Major et al., "Mechanisms of ZnII-activated magnetic resonance imaging agents," Inorg Chem, 2008, 47(22):10788-10795.
Major et al., "The synthesis and in vitro testing of a zinc-activated MRI contrast agent," PNAS, 2007, 104(35):13881-13886.
Manus et al., "Gd(III)-nanodiamond conjugates for MRI contrast enhancement," Nano Lett., 2010, 10(2):484-489.
Matosziuk et al., "Synthesis, Characterization, and in vitro Testing of a Bacteria-Targeted MR Contrast Agent," Eur J Inorg Chem, 2012, 2012(12):2099-2107.
Matthews et al., "Non-invasive imaging in experimental medicine for drug development," Curr Opin Pharmacol., 2011, 11(5):501-507.
Matthews et al., "Positron emission tomography molecular imaging for drug development," Br J Clin Pharmacol., 2012, 73(2):175-186.
Moats et al., "A 'Smart' Magnetic Resonance Imaging Agent That Reports on Specific Enzymatic Activity," Angew Chem Int Ed Engl., 1997, 36(7):726-728.
Ning et al., "Maltodextrin-based imaging probes detect bacteria in vivo with high sensitivity and specificity," Nat Mater, 2011, 10(8):602-607.
Ono et al., "Molecular approaches to the treatment, prophylaxis, and diagnosis of Alzheimer's disease: novel PET/SPECT imaging probes for diagnosis of Alzheimer's disease," J Pharmacol Sci., 2012, 118(3):338-344.
Ostrov et al., "Molecular imaging of inflammation and carcinogenesis," Cancer Prey Res, 2011, 4(10):1523-1526.
Pien et al., "The clinical and prognostic importance of positive blood cultures in adults," Am J Med, 2010, 123(9):819-828.
Pourakbari et al., "Evaluation of procalcitonin and neopterin level in serum of patients with acute bacterial infection," Braz J Infect Dis, 2010, 14(3):252-255.
Que et al., "A copper-activated magnetic resonance imaging contrast agent with improved turn-on relaxivity response and anion compatibility," Dalton Trans., 2010, (2):469-476.
Que et al., "A smart magnetic resonance contrast agent for selective copper sensing," J Am Chem Soc., 2006, 128(50):15942-15943.
Quici et al., "Visible and near-infrared intense luminescence from water-soluble lanthanide [Tb(III), Eu(III), Sm(III), Dy(III), Pr(III), Ho(III), Yb(III), Nd(III), Er(III)] complexes," Inorg Chem, 2005, 44(3):529-537.
Rayes et al., "Supply of pre- and probiotics reduces bacterial infection rates after liver transplantation—a randomized, double-blind trial," Am J Transplant, 2005, 5(1):125-130.
Robles et al., "Molecular imaging true-colour spectroscopic optical coherence tomography," Nat Photonics, 2011, 5(12):744-747.
Singh et al., "Application of molecular techniques to the study of hospital infection," Clin Microbiol Rev, 2006, 19(3):512-530.
Song et al., "Multimodal Gadolinium-Enriched DNA—Gold Nanoparticle Conjugates for Cellular Imaging," Angew. Chem. Int. Ed., 2009, 48: 9143-9147.
Song et al., "Synthesis of multimeric MR contrast agents for cellular imaging," J Am Chem Soc, 2008, 130(21):6662-6663.
Strauch et al., "Reporter protein-targeted probes for magnetic resonance imaging," J Am Chem Soc, 2011, 133(41):16346-16349.
Sukerkar et al., "A steroid-conjugated magnetic resonance probe enhances contrast in progesterone receptor expressing organs and tumors in vivo," Mol Pharm, 2011, 8(4):1390-1400.
Sukerkar et al., "Synthesis and biological evaluation of water-soluble progesterone-conjugated probes for magnetic resonance imaging of hormone related cancers," Bioconjug Chem, 2011, 22(11):2304-2316.
Surman et al., "A pyrophosphate-responsive gadolinium(III) MRI contrast agent," Chem Eur J., 2011, 17(1):223-230; S223/221-S223/216.
Urbanczyk-Pearson et al., "Mechanistic investigation of beta-galactosidase-activated MR contrast agents," Inorg Chem., 2008, 47(1):56-68.
Waldman et al., "Quantitative imaging biomarkers in neuro-oncology," Nat Rev Clin Oncol., 2009, 6(8):445-454.
Wang et al., "Fluorescent nanoparticles for multiplexed bacteria monitoring," Bionconjug Chem, 2007, 18(2):297-301.
Zhang et al., "Synthesis and biodistribution of a novel ($^{99}$m)TcN complex of norfloxacin dithiocarbamate as a potential agent for bacterial infection imaging," Bioconjug Chem, 201, 22(3):369-375.

* cited by examiner

BACTERIA-TARGETED MAGNETIC RESONANCE CONTRAST AGENTS

The present application claims priority to U.S. Provisional application Ser. No. 61/779,115, filed Mar. 13, 2013, which is herein incorporated by reference in its entirety.

STATEMENT REGARDING GOVERNMENT FUNDING

This invention was made with government support under R01 EB005866-01 awarded by the National Institutes of Health. The government has certain rights in the invention.

FIELD OF THE INVENTION

The present invention relates to bacteria-targeted contrast agents for magnetic resonance imaging (MRI). In particular, the present invention relates to bacteria targeted MRI contrast agents that can be used to detect bacteria in vivo or in vitro. In certain embodiments, the contrast agents comprise a metal chelate conjugated to at least two Zn-dipicolylamine groups.

BACKGROUND OF THE INVENTION

With the advancement of medical treatments and technologies, bacterial infection has become a growing concern in the course of patient care.[1] In the United States, approximately 2 million hospital patients develop a hospital-acquired infection each year.[1] Due to illness, organ transplantation, or specific disease treatments, many patients possess a depressed immune system that renders the individual more susceptible to infection. [2] Further, prosthetic materials such as stents, mesh grafts, and catheters can provide additional microenvironments for bacterial growth. [3] Antibiotic-resistant bacteria strains increase the severity of illness, length of hospital stay and mortality from infection.[4] Consequently, new agents and techniques to prevent, diagnose, and treat bacterial infection are needed.

Typically an accurate diagnosis of bacterial infection is derived from cultures of samples obtained from the site of suspected infection. Other clinical methods to identify infection include monitoring of body temperature, white blood cell count, erythrocyte sedimentation rate and cytokine reactions—none of which are a specific response to infection.[5] Consequently, these tests cannot differentiate between bacterial infection and sterile inflammation, and are prone to false positive results due to contamination.[6]

As a result, there is a need to develop molecular imaging probes that can specifically identify bacterial infection, monitor therapeutic response, and ultimately guide clinical decisions. Additionally, bacteria-specific contrast agents could aid in the study of infection pathology. Bacteria-targeted imaging probes would allow for in vivo monitoring of both infection progression and antibiotic effectiveness (e.g., in animal models). This could lead to the development of new antibiotics capable of targeting bacterial strains that have developed resistance to current medications.

SUMMARY OF THE INVENTION

The present invention relates to bacteria-targeted contrast agents for magnetic resonance imaging (MRI). In particular, the present invention relates to bacteria targeted MRI contrast agents that can be used to detect bacteria in vivo or in vitro. In certain embodiments, the contrast agents comprise a metal chelate conjugated to at least two Zn-dipicolylamine groups.

In some embodiments, the present invention provides compositions comprising a contrast agent comprising a metal chelate conjugated to at least two Zn-dipicolylamine groups. In certain embodiments, the contrast agent comprises a chemical structure shown in Formula (I), (II), or (III) below:

Formula (I)

Formula (II)

and

Formula (III)

wherein M is a metal ion, and wherein R is a linker moiety.

In some embodiments, the present invention provides pharmaceutical compositions comprising: a) a contrast agent comprising a metal chelate conjugated to at least two Zn-dipicolylamine groups; and b) one or more pharmaceutically acceptable adjuvants, excipients or diluents for use in enhancing image contrast in in vivo imaging or for treatment of a disease. In certain embodiments, the contrast agent comprises a chemical structure shown in Formula (I), (II), or (III) below:

Formula (I)

Formula (II)

Formula (III)

wherein M is a metal ion, and wherein R is a linker moiety.

In certain embodiments, the metal ion is selected from the group consisting of Gd, Eu, Cu, Mn, Fe, Dy, Tb, Tm, Yb, Er, Ho, Cr, V, and Co. In particular embodiments, the metal ion is Eu or Gd. In further embodiments, R is a divalent branched or unbranched carbon chain comprising from about 2 to about 30 carbon atoms. In certain embodiments, $R=(CH_2)_n$, where n=1 or 2.

The present invention is not limited by the metal chelate employed. In some embodiments, the metal chelate is the metal chelate used in the following contrast agents: gadoterate (Dotarem), gadodiamide (Omniscan), gadobenate (MultiHance), gadopentetate (Magnevist, Magnegita, Gado-MRT ratiopharm), gadoteridol (ProHance), gadoversetamide (OptiMARK), gadofosveset (Ablavar, formerly Vasovist), gadoxetate (Primovist), or gadobutrol (Gadovist), the metal chelate shown in Formula (I), or a macrocyclic GdIII chelate.

In some embodiments, the contrast agent is as follows:

In other embodiments, the contrast agent is as follows:

In some embodiments, the present invention provides methods for imaging of bacteria in a subject comprising: a) administering a contrast agent as describe herein to a subject suspected of having a bacterial infection, and b) performing imaging of the subject and detecting a signal from the contrast agent if the subject is infected with bacteria (e.g., wherein the contrast agent provides a location in the subject where the bacteria are located or are concentrated).

In certain embodiments, the present invention provides methods for imaging of bacteria in a sample comprising: a) contacting a contrast agent as disclosed herein with a biological sample suspected of having bacteria, and b) performing imaging of said sample and detecting a signal from said contrast agent if the sample has the bacteria.

In further embodiments, the bacteria comprises *E. coli*. In further embodiments, the bacteria comprises *Staphylococcus* type bacteria, *Haemophilus influenzae*, *Chlamydia trachomatis*, *Neisseria* bacteria, or *Streptococcus* bacteria. In particular embodiments, the imaging comprises magnetic resonance imaging.

DESCRIPTION OF FIGURES

FIG. 1.

FIG. 4.

FIG. 5. In vitro cellular labeling of *S. aureus* and *E. coli* with Zn-1, Zn-2, and Zn-3. *S. aureus* (5A) or *E. coli* (5B) were incubated with increasing concentrations of Zn-1 (black bars), Zn-2 (gray bars), or Zn-3 (white bars) at room temperature in LB broth. GdIII content was analyzed by ICP-MS and is represented as the total amount of GdIII per sample. Data are represented as the means±SEM.

FIG. 6. *S. aureus* cultures were incubated with 300 μm Zn-1, Zn-2 or Zn-3. Cells were washed 3 times with LB-broth and resuspended in 1% agarose. Scale bar represents 300 μm. FIG. 6A: T1-weighted map was acquired at 7 T at 25° C. (TR/TE=500/11 ms). Cells labeled with Zn-1 are clearly brighter than both unlabeled bacteria and bacteria treated with Zn-2 or Zn-3. FIG. 6B: T1 relaxation times of agarose suspensions of *S. aureus* were measured using a saturation recovery pulse sequence with an echo time (TE) of 11 ms and repetition times (TR) as indicated in the Experimental Procedures at 7 T and 1.41 T. Data are presented as the percent reduction in T1 vs. bacteria incubated with LB media, washed, and suspended in agarose.

DETAILED DESCRIPTION OF THE INVENTION

The present invention provides bacteria-targeted contrast agents for magnetic resonance imaging (MRI). In particular, the present invention relates to bacteria targeted MRI contrast agents (e.g., those shown in Formula I, Formula II, and Formula II) that can be used to detect bacteria in vivo or in vitro. In certain embodiments, the contrast agents comprise a metal chelate conjugated to at least two Zn-dipicolylamine groups.

Figure 1:
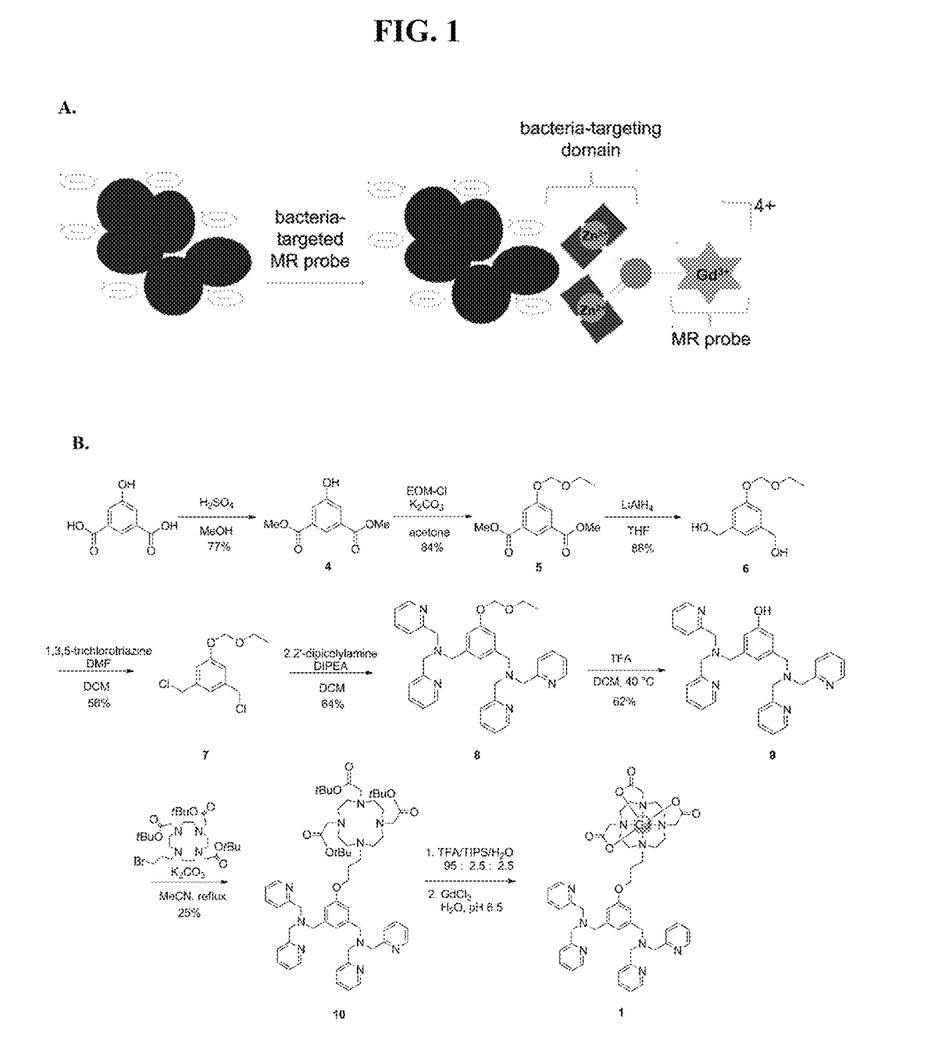
FIG. 1A shows a schematic of a bacteria targeted contrast agent with two bacteria-targeted Zn-dpa domains that are conjugated to a macrocyclic GdIII chelate. While the present invention is not limited to any particular mechanism, and an understanding of the mechanism is not necessary to practice the invention, it is believed that the contrast agents affinity for bacteria is due to the electrostatic attraction between the anionic bacteria membrane and the positive charge of the Zn-dpa moieties.
FIG. 1B shows synthesis of the bacteria-targeted MR contrast agent 1 (Zn-1) that contains two dipicolyl moieties, each of which is capable of binding one ZnII ion to give the final ZnII-bound complex an overall charge of 4+. The europium and terbium analogues were synthesized in a similar manner, using $EuCl_3$ and $Tb(OAc)_3$ in place of $Gd(OAc)_3$.
Figure 2:
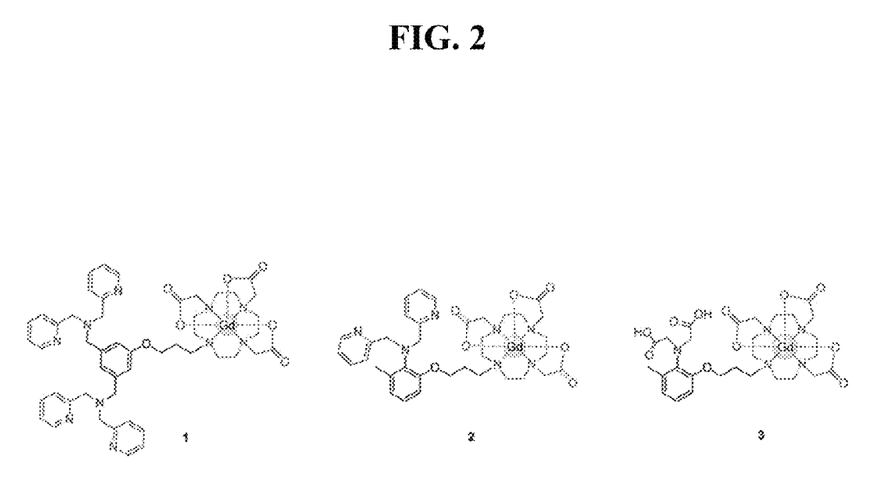
FIG. 2 shows structures of complexes used for bacteria labeling studies in Example 2. After the addition of ZnII, Zn-1 and Zn-2 have charges of 4+ and 2+, respectively, while Zn-3 is charge neutral.[16]

In certain embodiments, the MRI contrast agent is Zn-1 (see "1" in FIG. 1). As described in the Examples below, in vitro studies with *S. aureus* and *E. coli* showed that Zn-1 exhibits a significant improvement in bacteria labeling efficiency vs. control. Studies with a structural analogue, Zn-2 (see "2" in FIG. 2), indicate that removal of one Zn-dpa moiety dramatically reduces the agent's affinity for bacteria. The ability of Zn-1 to significantly reduce the T1 of labeled vs. unlabeled bacteria, resulting in enhanced MR image contrast, demonstrates its useful properties for visualizing bacterial infections in vivo.

The present invention is not limited by the linker moiety (R) shown in Formulas (I) and (II). In one embodiment the linker is an amino acid. In another embodiment, the linker is a peptide. In another embodiment, the linker is a divalent branched or unbranched carbon chain comprising from about 2 to about 30 carbon atoms, which chain optionally includes one or more (e.g., 1, 2, 3, or 4) double or triple bonds, and which chain is optionally substituted with one or more (e.g., 2, 3, or 4) hydroxy or oxo (=O) groups, wherein one or more (e.g., 1, 2, 3, or 4) of the carbon atoms in the chain is optionally replaced with a non-peroxide —O—, —S— or —NH— and wherein one or more (e.g., 1, 2, 3, or 4) of the carbon atoms in the chain is replaced with an aryl or heteroaryl ring. In another embodiment, the linker is a divalent branched or unbranched carbon chain comprising from about 2 to about 30 carbon atoms, which chain optionally includes one or more (e.g., 1, 2, 3, or 4) double or triple bonds, and which chain is optionally substituted with one or more (e.g., 2, 3, or 4) hydroxy or oxo (=O) groups, wherein one or more (e.g., 1, 2, 3, or 4) of the carbon atoms in the chain is replaced with a non-peroxide —O—, —S— or —NH— and wherein one or more (e.g., 1, 2, 3, or 4) of the carbon atoms in the chain is replaced with one or more (e.g., 1, 2, 3, or 4) aryl or heteroaryl rings.

In another embodiment, the linker is a divalent branched or unbranched carbon chain comprising from about 2 to about 30 carbon atoms, which chain optionally includes one or more (e.g., 1, 2, 3, or 4) double or triple bonds, and which chain is optionally substituted with one or more (e.g., 2, 3, or 4) hydroxy or oxo (=O) groups, wherein one or more (e.g., 1, 2, 3, or 4) of the carbon atoms in the chain is replaced with a non-peroxide —O—, —S— or —NH— and wherein one or more (e.g., 1, 2, 3, or 4) of the carbon atoms in the chain is replaced with one or more (e.g., 1, 2, 3, or 4) heteroaryl rings. In another embodiment, the linker is a divalent branched or unbranched carbon chain comprising from about 2 to about 30 carbon atoms, which chain optionally includes one or more (e.g., 1, 2, 3, or 4) double or triple bonds, and which chain is optionally substituted with one or more (e.g., 2, 3, or 4) hydroxy or oxo (=O) groups, wherein one or more (e.g., 1, 2, 3, or 4) of the carbon atoms in the chain is optionally replaced with a non-peroxide —O—, —S— or —NH—. In another embodiment, the linker is a divalent group of the formula —W—F—W— wherein F is $(C_1$-$C_{30})$alkyl, $(C_2$-$C_{30})$alkenyl, $(C_2$-

$C_{30}$)alkynyl, ($C_3$-$C_8$)cycloalkyl, or ($C_6$-$C_{10}$), wherein W is —N(Q)C(=O)—, —C(=O)N(Q)-, —OC(=O)—, —C(=O)O—, —O—, —S—, —S(O)—, —S(O)$_2$—, —N(Q)-, —C(=O)—, or a direct bond; wherein each Q is independently H or ($C_1$-$C_6$)alkyl.

In another embodiment, the linker is a divalent branched or unbranched carbon chain comprising from about 2 to about 30 carbon atoms, which chain optionally includes one or more (e.g., 1, 2, 3, or 4) double or triple bonds, and which chain is optionally substituted with one or more (e.g., 2, 3, or 4) hydroxy or oxo (=O) groups. In another embodiment, the linker is a divalent branched or unbranched carbon chain comprising from about 2 to about 30 carbon atoms, which chain optionally includes one or more (e.g., 1, 2, 3, or 4) double or triple bonds. In another embodiment, the linker is a divalent branched or unbranched carbon chain comprising from about 2 to about 30 carbon atoms. In another embodiment, the linker is a divalent branched or unbranched carbon chain comprising from about 2 to about 20 carbon atoms, which chain optionally includes one or more (e.g., 1, 2, 3, or 4) double or triple bonds, and which chain is optionally substituted with one or more (e.g., 2, 3, or 4) hydroxy or oxo (=O) groups. In another embodiment, the linker is a divalent branched or unbranched carbon chain comprising from about 2 to about 20 carbon atoms, which chain optionally includes one or more (e.g., 1, 2, 3, or 4) double or triple bonds. In another embodiment, the linker is a divalent branched or unbranched carbon chain comprising from about 2 to about 20 carbon atoms. In another embodiment, the linker is —(CH$_2$CH$_2$O)$_{1-10}$.

In another embodiment, the linker is —C(=O)NH(CH$_2$)$_3$—; —C(=O)NH(CH$_2$)$_5$C(=O)NH(CH$_2$)—; or —CH$_2$OC(=O)NH(CH$_2$)$_2$—O—(CH$_2$)$_2$—O—(CH$_2$)—.

In another embodiment, the linker comprises one or more divalent heteroaryl groups. Specifically, ($C_1$-$C_{30}$)alkyl can be methyl, ethyl, propyl, isopropyl, butyl, iso-butyl, sec-butyl, pentyl, 3-pentyl, hexyl, heptyl, octyl, nonyl, or decyl; ($C_3$-$C_8$)cycloalkyl can be cyclopropyl, cyclobutyl, cyclopentyl, or cyclohexyl; ($C_2$-$C_{30}$)alkenyl can be vinyl, allyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, 5-hexenyl, heptenyl, octenyl, nonenyl, or decenyl; ($C_2$-$C_{30}$)alkynyl can be ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl, heptynyl, octynyl, nonynyl, or decynyl; ($C_6$-$C_{10}$)aryl can be phenyl, indenyl, or naphthyl; and heteroaryl can be furyl, imidazolyl, triazolyl, triazinyl, oxazoyl, isoxazoyl, thiazolyl, isothiazoyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide) or quinolyl (or its N-oxide). The term aromatic includes aryl and heteroaryl groups.

EXAMPLES

Example 1

Synthesis of Zn-1 and an Eu Analogue

This Example describes the synthesis of MR contrast agent Zn-1 (aka 1), as well as the Eu analogue termed 1-Eu. A summary of the synthesis procedure is as follows, and is shown in FIG. 1B. The synthesis of 1 (Zn-1) begins with methylation of the carboxylic acids of 5-hydroxyisophthalic acid to give the diester 4, in accordance with literature procedures (Scheme 1).[17] The phenol was protected with ethoxymethyl chloride and the esters reduced with lithium aluminum hydride to produce the diol 6. The alcohol groups were converted to chlorides using trichlorotriazine and DMF to form the dichloride 7.[18] Displacement of the chlorides with dipicolylamine gave the protected, bis-dpa compound 8. The phenol was deprotected with trifluoroacetic acid (TFA) in dichloro-methane to give 9 in nearly quantitative yield. The bis-dpa phenol 9 was allowed to react with a bromoalkane derivative of tris-tert-butyl-protected DO3A to give the final, protected ligand 10. Deprotection of the tert-butyl groups with TFA and subsequent metallation with Gd(OAc)$_3$, yielded the final compound 1, which was purified by semi preparative HPLC.

The detailed protocol for synthesis for Zn-1 is as follows.

Synthesis of Zn-1: Chloromethyl ethyl ether and 2,2'-dipicolylam-ine were obtained from TCI America. All other chemicals were obtained from Sigma Aldrich and used without further purification. EMD 60F 254 silica gel plates were used for thin layer chromatography and visualized using UV light, iodoplatinate stain, or cerium ammonium molybdate (CAM) stain. Column chromatography was performed using standard grade 60 Å 230-400 mesh silica gel (Sorbent Technologies). Unless otherwise noted, 1H and $^{13}$C NMR were obtained on a Bruker Avance III 500 MHz NMR Spectrometer. A Varian 1200 L single-quadrupole mass spectrometer was used to acquire electrospray ionization mass spectra (ESI-MS). Semi-preparative HPLC was performed on a Waters 19×250 mm Atlantis C18 Column. Analytical HPLC-MS was performed using a Waters 4.6×250 mm 5 μm Atlantis C18 column using the Varian Prostar 500 system equipped with a Varian 380 LC ELSD system, a Varian 363 fluorescence detector, and a Varian 335 UV/Vis detector. $^1$H NMR of 1-Eu as a function of ZnII concentration was performed on a Bruker Avance III 600 MHz spec-concentration was performed on a Bruker Avance III 600 MHz spectrometer at 60° C. in d6-DMSO. Dimethyl 5-hydroxyisophthalate (4) was synthesized according to literature procedure.[17]

Dimethyl 5-(Ethoxymethoxy)isophthalate (5): To a solution of 4 (4.42 g, 21 mmol) in acetone (50 mL) was added K2CO3 (11.5 g, 84 mmol). The reaction was cooled to 0° C., and chloromethylethyl ether (2.74 g, 29 mmol) was added. After 12 h, TLC (30% ethyl acetate/hexanes) confirmed completion of the reaction. The reaction mixture was filtered and the solvent evaporated. The residue was purified on a silica gel column, eluting with 15% ethyl acetate/hexanes, to give 4.72 g of product as a white solid (84% yield). 1H NMR (500 MHz, CDCl3): δ=8.29 (t, J=1.5 Hz, 1 H, Haryl), 7.84 (d, J=1.5 Hz, 2 H, Haryl), 5.27 (s, 2 H, O—CH2-O), 3.91 (s, 6 H, O—CH3), 3.71 (q, J=7.0 Hz, 2 H, CH2CH3), 1.19 (t, J=7.1 Hz, 3 H, CH2CH3) ppm. $^{13}$C NMR (126 MHz, CDCl3): δ=166.08 (COOMe), 157.38 (Car-OCH2), 131.83 (Car-COOMe), 124.00 (Car), 121.55 (Car), 93.14 (O—CH2-O), 64.68 (CH2-CH3), 52.48 (COOCH3), 15.12 (CH3) ppm.

[5-(Ethoxymethoxy)-1,3-phenylene]dimethanol (6): Lithium aluminum hydride (1.22 g, 32.8 mmol) was suspended in THF (50 mL), and the mixture cooled to 0° C. A solution of 5 (4 g, 14.9 mmol) in THF (40 mL) was added dropwise to the LAH suspension. After 2 h, completion of the reaction was confirmed by TLC (5% MeOH/DCM). The reaction was quenched with 15 mL of water. The reaction mixture was filtered and the solvent evaporated. The residue was brought up in ethyl acetate and washed with water and brine. The organic layer was dried with Na2SO4, filtered, and the solvent evaporated to give 2.63 g of product as a white, oily solid (83% yield). 1H NMR (500 MHz, CDCl3):

δ=6.99 (s, 1 H, Har), 6.94 (d, J=1.4 Hz, 2 H, Har), 5.22 (s, 2 H, O—CH2-O), 4.64 (d, J=3.7 Hz, 4H, CH2-OH), 3.72 (q, J=7.0 Hz, 2 H, CH2CH3), 2.15 (s, 2 H, OH), 1.22 (t, J=7.1 Hz, 3 H, CH2CH3) ppm. 13C NMR (126 MHz, CDCl3): δ=157.85 (Car-OCH2), 142.97 (Car-CH2OH), 118.73 (Car), 113.92 (Car), 93.15 (O—CH2-O), 65.15 (CH2-OH), 64.51 (CH2CH3), 15.23 (CH2-CH3) ppm.

1,3-Bis(chloromethyl)-5-(ethoxymethoxy)benzene (7): Trichlorotriazine (4.35 g, 23.58 mmol) was dissolved in DMF (10 mL) at room temperature and allowed to stir for one hour until the formation of a yellow precipitate was observed. A solution of 6 (2 g, 9.43 mmol) in DCM (30 mL) was added and the reaction allowed to stir overnight at room temperature. After confirming completion of the reaction by TLC (15% ethyl acetate/hexanes), the reaction mixture was transferred to a reparatory funnel and washed successively with water, a saturated solution of Na2CO3, and brine. The organics were dried with Na2SO4, filtered and the solvent evaporated. The residue was adsorbed to silica and purified on a silica gel column, eluting with 5% ethyl acetate/hexanes to give 1.29 g of product as a clear oil (55% yield). 1H NMR (500 MHz, CDCl3): δ=7.06 (d, J=1.5 Hz, 1 H, Har), 7.03 (d, J=1.6 Hz, 2 H, Har), 5.24 (s, 2H, O—CH2-O), 4.54 (s, 4H, CH2-Cl), 3.73 (q, J=7.1 Hz, 2 H, CH2-CH3), 1.23 (t, J=7.1 Hz, 3 H, CH2-CH3) ppm. $^{13}$C NMR (126 MHz, CDCl$_3$): δ=157.85 (Car-OCH2), 139.38 (Car-CH2Cl), 121.96 (Car), 116.37 (Car), 93.15 (O—CH2-O), 64.46 (CH2CH3), 45.76 (CH2Cl), 15.13 (CH2CH3) ppm.

[5-(Ethoxymethoxy)benzene-1,3-diyl]bis[N,N-bis(pyridin-2-ylmethyl)methanamine] (8): DIEA (1.74 g, 13.5 mmol) and 2,2-dipicolylamine were stirred in DCM (10 mL) for 10 min. A solution of 7 in DCM (10 mL) was added and the reaction allowed to stir at room temperature. After 4 d, completion of the reaction was confirmed by MS. The solvent was evaporated and the residue purified on a silica column eluting with 4% methanol/chloroform to give 3.5 g of product as a yellow oil (99% yield). 1H NMR (500 MHz, CDCl3): δ=8.48 (dd, J=3.8, 2.3 Hz, 4 H, o-Hpy), 7.66-7.54 (m, 8 H, Hpy), 7.11 [td, J=5.1, 3.3 Hz, 5 H, Hpy (4 H), Har (1 H)], 7.02 (d, J=1.4 Hz, 2 H, Har), 5.20 (s, 2 H, O—CH2-O), 3.78 (s, 8 H, N—CH2-Cpy), 3.71 (q, J=7.1 Hz, 2 H, CH2-CH3), 3.63 (s, 4 H, Car-CH2-N), 1.19 (t, J=7.1 Hz, 3 H, CH2CH3) ppm. 13C NMR (126 MHz, CDCl$_3$): δ=159.88 (CH2-o-Cpy-Npy), 157.74 (Car-OCH2), 149.02 (o-Cpy-Npy), 140.85 (Car-CH2N), 136.53 (c-Cpy), 122.78 (m-Cpy), 122.44 (Car), 122.04 (m-Cpy), 115.12 (Car), 93.32 (O—CH2-O), 64.27 (CH2CH3), 60.16 (N—CH2-Cpy), 58.57 (Car-CH2-N), 15.26 (CH2CH3) ppm. MS (ESI-positive): m/z=575.3 [M+], 597.3 [M+Na+].

3,5-Bis{[bis(pyridin-2-ylmethyl)amino]methyl}phenol (9): A solution of 8 (2.21 g, 3.84 mmol) in DCM was heated to 40° C. Trifluoroacetic acid (2.38 mL, 23 mmol) was added and the reaction allowed to stir for 12 h (monitored by TLC: 10% methanol/DCM). The protonated product was extracted from DCM with water. The aqueous layer was neutralized and the product extracted into DCM. The organic layers were combined, dried with Na2SO4, filtered and the solvent evaporated to give 1.73 g of product as a yellow oil. 1H NMR (500 MHz, CDCl3): δ=8.52-8.40 (m, 4 H, o-Hpy), 7.65-7.54 (m, 8 H, Hpy), 7.12 (td, J=5.7, 2.4 Hz, 4 H, Hpy), 7.02 (s, 1 H, Har), 6.79 (d, J=1.2 Hz, 2 H, Har), 3.77 (s, 8 H, N—CH2-Cpy), 3.56 (s, 4 H, Car-CH2-N), 2.60-2.20 (m, 1 H, OH) ppm. 13C NMR (126 MHz, CDCl3): δ=159.88 (CH2-Cpy-Npy), 157.57 (Car-OH), 148.80 (o-Cpy), 140.74 (Car-CH2N), 136.86 (p-Cpy), 123.03 (m-Cpy), 122.24 (m-Cpy), 120.07 (Car), 114.86 (Car), 60.05 (N—CH2-Cpy), 58.77 (Car-CH2-N) ppm. MS (ESI-positive): m/z=517.2 [M+], 539.2 [M+Na+].

Tri-tert-butyl 10-[3-(3,5-Bis{[bis(pyridin-2-ylmethyl)amino]methyl}-phenoxy)propyl]-1,4,7,10-tetraazacyclododecane-1,4,7-tricarboxylate(10): Tri-tert-butyl 10-(3-bromopropyl)-1,4,7,10-tetraazacyclododecane-1,4,7-tricarboxylate (tris-tert-butyl-DO3A) was synthesized by reacting tris-tert-butyl-DO3A with a large excess of 1,3-dibromopropane. K2CO3 (1.85 g, 13.48 mmol) and dibromopropane (3.4 mL, 30.36 mmol) were dissolved in acetonitrile (400 mL) and cooled to 0° C. Tris-tert-butyl-DO3A (2 g, 3.36 mmol), synthesized according to literature procedure, was dissolved in acetonitrile (50 mL) and added to the above solution via dropping funnel. Reaction progress was monitored by MS. After three days the reaction was filtered, the solvent evaporated, and the crude product run on a silica gel column, eluting with 2-4% methanol in DCM. The bromopropyl-DO3A was added to a solution of K2CO3 (1.25 g, 9.05 mmol) and 9 (937 mg, 1.81 mmol) in acetonitrile (60 mL). The reaction was heated to 70° C. and allowed to reflux under nitrogen for 48 h. The reaction mixture was filtered and the solvent evaporated. The crude product was purified on a silica gel column, eluting with 7-10% methanol in chloroform to give 460 mg of yellow oil (25% yield). 1H NMR (500 MHz, CDCl3): δ=8.51 (dt, J=4.9, 1.4 Hz, 4 H, o-Hpy), 7.75-7.52 (m, 8 H, Hpy), 7.15 [ddd, J=6.9, 4.8, 1.5 Hz, 5 H, 4 Hpy (4 H), Har (1 H)], 6.75 (d, J=1.5 Hz, 2 H, Har), 3.92 (s, 2 H, CH2-CH2-OH), 3.79 (s, 8 H, N—CH2-Cpy), 3.64 (s, 4 H, Car-CH2-N), 3.41-1.80 [m, 26 H, N—CH2-CH2-N (16 H), N—CH2-COOH (6 H), N—CH2-CH2-CH2 (4 H)], 1.44 (d, J=9.8 Hz, 27 H) ppm. 13C NMR (126 MHz, CDCl3): δ=172.68 (COO-tBu), 171.77 (COO-tBu), 158.68 (CH2-Cpy-Npy), 157.96 (Car-OCH2), 148.01 (o-Cpy), 139.57 (Car-CH2-N), 135.56 (p-Cpy), 121.76 (m-Cpy), 121.10 (m-Cpy), 120.50 (Car), 112.46 (Car), 81.76 (O—C—CH3), 81.45 (O—C—CH3), 80.91 (O—C—CH3), 65.29 (O—CH2-CH2), 59.03 (N—CH2-Cpy), 57.65 (Car-CH2-N), 55.64 (N—CH2-CH2-N), 54.86 (N—CH2-CH2-N), 49.48 (N—CH2-COOH), 27.17 (C—CH3), 27.03 (C—CH3), 26.87 (C—CH3), 25.18 (CH2-CH2-CH2) ppm. MS (ESI-positive): m/z=1071 [M+], 1093 [M+Na+], 547.6 [(M++Na+)/2], 558.3 [(M+2Na+)/2], 573.4 [(M+Na++K+)/2], 595.3 [(M+3K+)/2].

Bis-dpa-Gd (1): The protected ligand 10 (338 mg, 0.315 mmol) was dissolved in a mixture of 95:2.5:2.5 TFA/triisopropylsilane/water and allowed to stir for four hours. The acid was evaporated under nitrogen. Removal of the tert-butyl protecting groups was confirmed by ESI-MS. The residue was brought up in water (5 mL) and the pH adjusted to 6.5 with NaOH (1 m). Gd(OAc)3 6 H2O (148 mg, 0.47 mmol) was added, and the solution allowed to stir at 50° C. for 4 d, adjusting the pH back to 6.5 with NaOH (1 m) as needed. The product was purified with reverse phase semi-preparative HPLC using a C18 column and eluting with a gradient of 0-100% acetonitrile in water over 35 min, tr=23 min. The purity and identity of the product was confirmed using analytical HPLC-MS on a C18 column, eluting with a gradient of 20-100% acetonitrile in water over 35 min, tr=19.5 min. The solvent was evaporated from pure fractions, and the residue brought up in DMSO and freeze dried. MS (ESI-positive) m/z=1058.3 [M+], 530.6 [M2+/2].

Bis-dpa-Eu (1-Eu): The same procedure was followed as for 1, using EuCl3.6H2O for metallation. Retention times were the same as for 1. MS (ESI-positive): m/z=1053.2 [M+] 527.2 [M2+/2].

Bis-dpa-Tb (1-Tb): The same procedure was followed as for 1, using Tb(OAc)3.6H2O for metallation. Retention times were the same as for 1. MS (ESI-positive): m/z=1059.2 [M+] 530.2 [M2+/2].

Luminesence Lifetime Measurements: The luminescence lifetime of a 200 mm solution of Zn-1-Tb was measured H2O and D2O on a Hitachi (San Francisco, Calif.) F4500 fluorimeter, using a λx=254 nm and λem=544 nm. Twenty-five scans were acquired, averaged and fit to a monoexponential decay function.

Characterization of Zn-1

Relaxation times (T1 and T2) of Zn-1 suspended in 1.0% (w/v) agarose (all subsequent bacterial samples were suspended in agarose) were measured at 1.41 (37° C.) and 7 T (25° C.) in order to provide data at both clinical and re-search field strengths. The r1 increases from 4.7 mm-1s-1 to 5.6 mm-1s-1 and the r2 increases from 9.0 mm-1s1 to 21.5 mm-1s1 at 1.41 T and 7 T respectively.

The hydration number, q, of Zn-1 was determined by comparing the fluorescence lifetimes of the TbIII analogue, Zn-1-Tb, in D2O and H2O. The fluorescence lifetimes were measured and fit to an exponential curve. The decay times, 1.06 ms in H2O and 1.89 ms in D2O, were related to the hydration number using Equation (1), giving a q value of 1.5.[19] The q value is an average measure of how many water molecules are directly bound to the lanthanide at a given time. The non-integer value of 1.5 indicates that that in solution, the complex coordinates either one or two inner sphere water molecules.

$$q = 4.2\left(\frac{1}{\tau_{H_2O}} - \frac{1}{\tau_{D_2O}} - 0.6\right) \quad (1)$$

Figure 3:
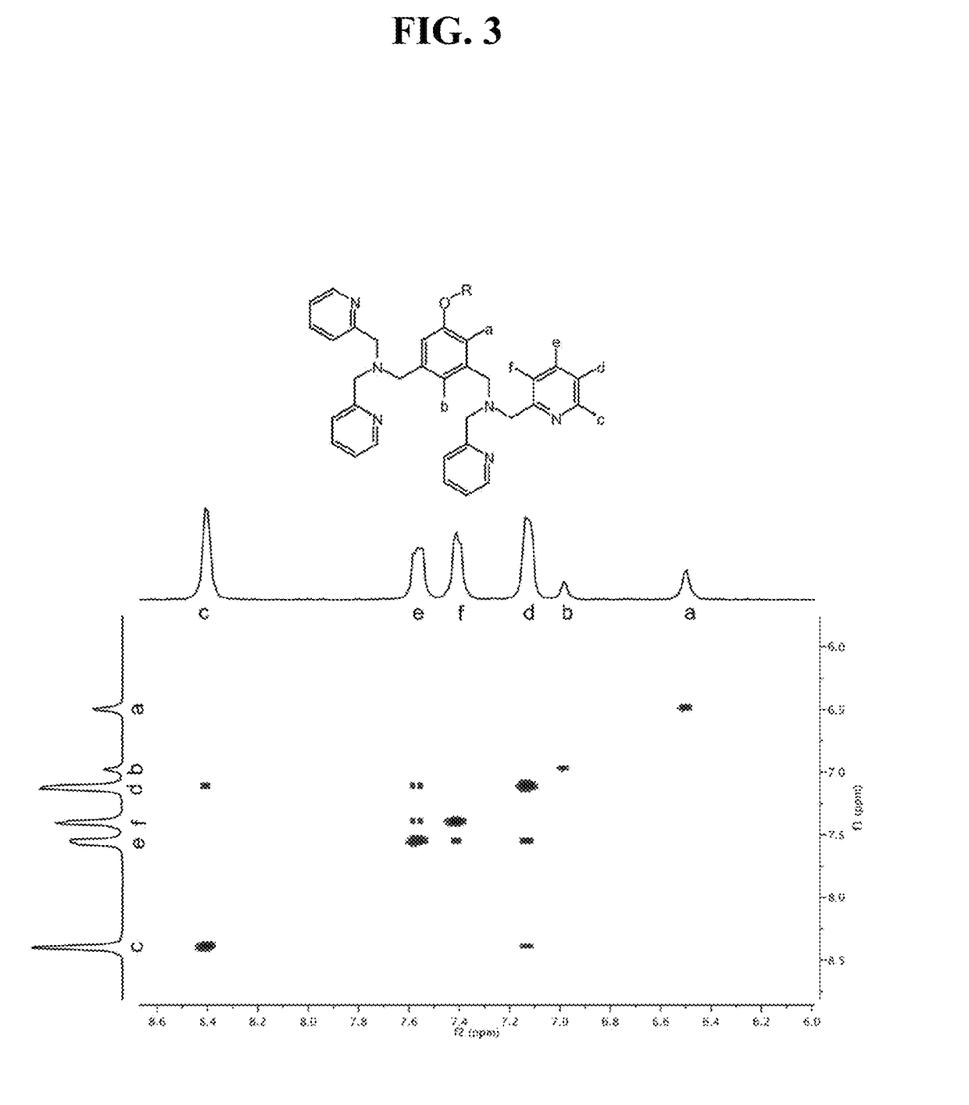
FIG. 3 shows the aromatic region of 1-Eu COSY spectrum (60° C., DMSO) used to assign peaks of the ZnII binding domains of 1. The addition of ZnII produces significant changes in the chemical shift of the protons on the ZnII binding domain until a ZnII:1-Eu ratio of 2 is reached.

1H NMR spectroscopy was used to confirm that 1 binds two ZnII ions per complex. The EuIII analogue of 1 (1-Eu) was synthesized and the 1H NMR chemical shifts of the dpa groups were monitored as ZnII was titrated into solution. The 1H peaks of the macrocycle and the propylene linker could not be assigned because the peaks are significantly broadened and shifted due to their proximity to the EuIII. However, there is enough separation between the lanthanide and the protons of the ZnII-binding dpa groups to make assignment possible, and a COSY spectrum was acquired to assign the aromatic dpa peaks (FIG. 3).

Figure 4:
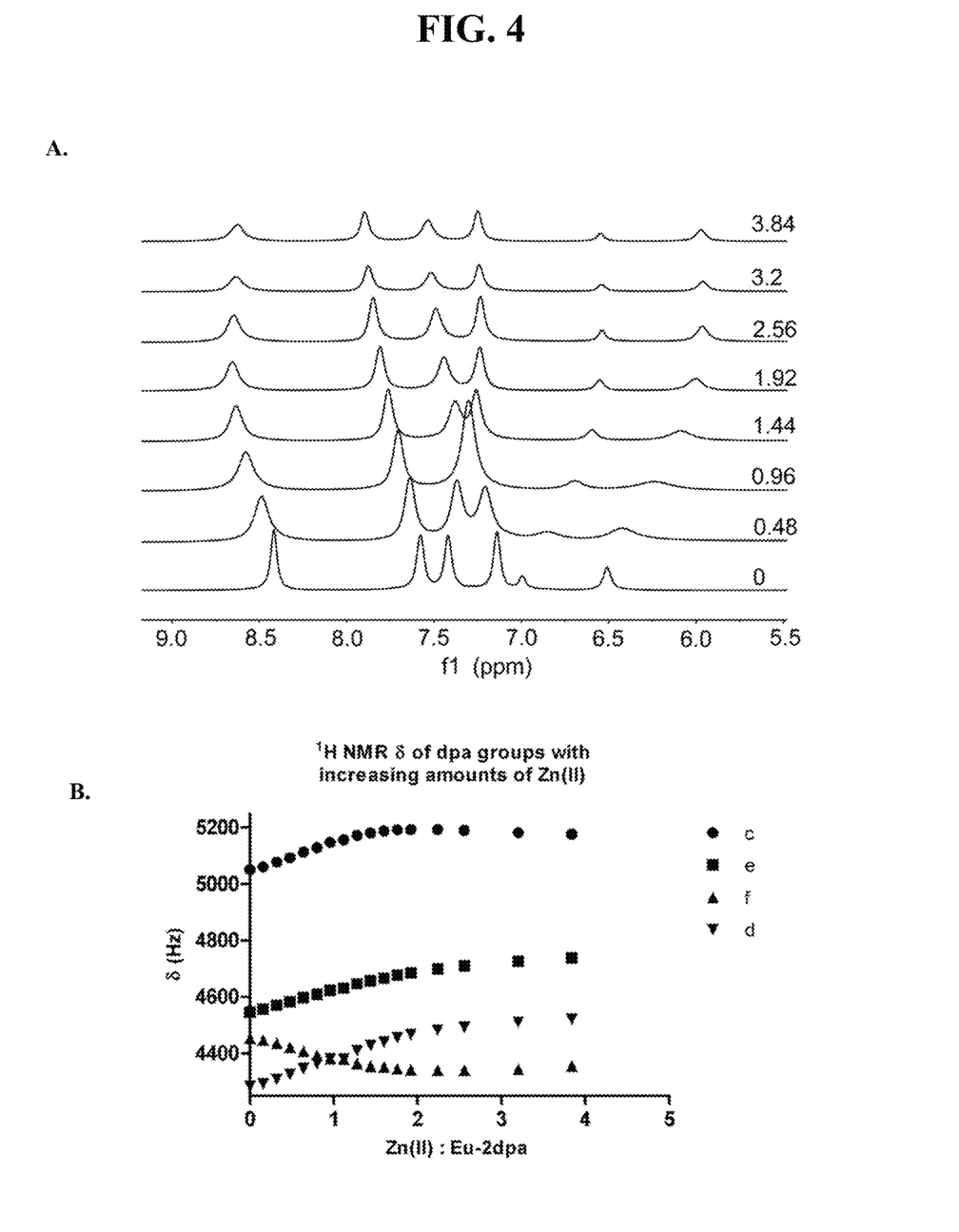
FIG. 4A shows the aromatic region of 1H NMR spectrum of Eu-1 with increasing amounts of ZnII.
FIG. 4B shows the chemical shift of peaks c, e, f, and d (see FIG. 3) as a function of ZnII/Eu-1 ratio. It is clear that the peaks of the ZnII binding domain shift only until a ZnII/Eu-1 ratio of 2 is obtained, confirming that each Eu-1 binds two ZnII ions.

ZnCl2 was added in 0.16 equiv. aliquots until a ZnII:1-Eu ratio of 3.82 was obtained. During the titration significant changes in the chemical shift of the dpa protons were observed until a ZnII:1-Eu ratio of 2 was reached. The addition of excess ZnII beyond this stoichiometry produced only negligible changes in chemical shift, confirming that 1-Eu binds two ZnII ions per complex (FIG. 4).

Example 2

Labeling of Bacteria with MRI Contrast Agents

This Example describes experiments conducted to use Zn-1, and controls Zn-2 (2) and Zn-3 (3), to specifically label bacteria.

Complexes 2 and 3 were synthesized and characterized as described previously.[16] Both 2 and 3 contain two flexible pendant arms capable of coordinating one ZnII ion. Zn-3 was used as a control for low-affinity binding to bacteria.

Materials and Methods:

Bacterial Culture: *Staphylococcus aureus* (29213) and *Escherichia coli* K-12 (29425) were obtained from ATCC (Rockville, Md.). Bacteria were grown from glycerol stocks, cultured in Luria-Bertani (LB) growth media with agitation overnight at 37° C. All experiments were performed after the bacteria had reached stationary phase to ensure that bacterial growth did not affect labeling efficiency. The optical density at 600 nm (OD600) was measured before and after labeling to confirm that the number of bacteria did not change significantly during the course of the experiment.

Quantification of Bacterial Cell Labeling by Inductively Coupled Plasma Mass Spectrometry (ICP-MS): Stock solutions (1 mm) of 1, 2, and 3 were prepared by dissolving each contrast agent in a solution of 2% DMSO in LB media. One molar equivalent of ZnCl2 was added to 2 and 3, while two molar equivalents of ZnCl2 were added to 1. The solutions were incubated at room temperature for 20 min (to form the ZnII-bound complexes), and were placed in a sonicating water bath (Branson 5510; Branson Ultrasonics, Danbury, Conn.) for an additional 10 min to ensure that all material was dissolved. The stock solutions were diluted to the desired concentrations with LB media.

*S. aureus* or *E. coli* cells were grown from a glycerol stock in LB media overnight. One mL aliquots of bacteria were taken and centrifuged at 6000 g for 3 min. The bacterial cell pellets were re-suspended in various concentrations of Zn-1, Zn-2 or Zn-3 and allowed to incubate at room temperature for 1 h while rotating. Bacteria were then centrifuged at 6000 g for 3 min, the supernatant was decanted, and the bacterial cell pellets were re-suspended in 1 mL LB media. This was repeated two more times for a total of three washes to remove any unbound contrast agent and decrease non-specific binding.

After washing, quantification of gadolinium was accomplished using inductively coupled plasma mass spectrometry (ICP-MS) of acid-digested samples. Specifically, bacterial cell pellets were digested in 100 μL of concentrated nitric acid (>69%, Sigma, St. Louis, Mo., USA) and placed at 70° C. for at least 12 h to allow for complete sample digestion. Ultra pure H2O (18.2 MΩ·cm) and multi-element internal standard containing Bi, Ho, In, Li(6), Sc, Tb, and Y (CLISS-1, Spex Certiprep, Metuchen, N.J., USA) were then added to produce a final solution of 3.0% nitric acid (v/v) and 5.0 ng/mL internal standard up to a total sample volume of 10 mL. Samples were then syringe filtered using 0.2 μm polyamide filters (Macherey-Nagel, Germany) into new 15 mL conical tubes. Individual Gd elemental standards were prepared at 1.00, 5.00, 10.0, 25.0, 50.0, 100, and 250 ng/mL concentrations with 3.0% nitric acid (v/v) and 5.0 ng/mL internal standards up to a total sample volume of 25 mL (using volumetric flasks).

ICP-MS was performed on a computer-controlled (Plasmalab software) Thermo X series II ICP-MS (Thermo Fisher Scientific, Waltham, Mass., USA) equipped with a CETAC 260 autosampler (Omaha, Nebr., USA). Each sample was acquired using 1 survey run (10 sweeps) and 3 main (peak jumping) runs (100 sweeps). The isotopes selected for analysis were 157,158Gd, and 115In and 165Ho (chosen as internal standards for data interpolation and machine stability).

Relaxation Time Measurements at 1.41 T: T1 and T2 relaxation times were measured on a Bruker mq60 NMR analyzer equipped with Minispec v. 2.51 Rev.00/NT software (Billerica, Mass., USA) operating at 1.41 T (60 MHz) and 37° C. T1 relaxation times were measured using an inversion recovery pulse sequence (t1_ir_mb) with the following parameters: four scans per point, 10 data points for fitting, mono-exponential curve fitting, phase cycling, 10 ms first pulse separation, and a recycle delay and final pulse separation greater than or equal to 5T1. T2 relaxation times were measured using a Carr-Purcell-Meiboom-Gill (CPMG) pulse sequence (t2_cp_mb) with the following parameters: four scans per point, mono-exponential curve fitting, phase cycling, 10 ms first pulse separation, 15 second recycle delay, 1 ms 90°-180° pulse separation (tau), while altering the number of data points to ensure accurate mono-exponential curve fitting (500-10000 data points for fitting). Relaxivities were determined by taking the slope of a plot of 1/T1 (s-1) or 1/T2 (s-1) vs. gadolinium concentration (mm) of each compound in either LB broth or in 1% (w/v) agarose.

MR Imaging and Relaxation Time Measurements at 7.05 T: All MR imaging was performed on an 89 mm bore size PharmaScan 7.05 T MR imaging spectrometer fitted with shielded gradient coils (Bruker BioSpin, Billerica, Mass., USA) using a RF RES 300 1H 089/023 quadrature transmit/receive mouse brain volume coil (Bruker BioSpin, Billerica, Mass., USA). All MR images were acquired using Paravision 5.0.1 software (Bruker BioSpin, Billerica, Mass., USA). S. aureus cultures were labeled with 300 µm Zn-1, Zn-2, and Zn-3 and then washed three times the LB broth as described previously. After the final wash samples were centrifuged at 6000 g for 3 min to pellet the bacteria, which were then suspended in 1.0% (w/v) low melting point agarose (Sigma, St. Louis, Mo.) in 7.5 mm outer diameter NMR tubes and incubated on ice to allow for gelation of the agarose. Samples were then positioned in a 23 mm mouse brain volume transmit/receive coil prior to imaging. T1-weighted images were acquired using a rapid-acquisition rapidecho variable-repetition time (RAREVTR) pulse sequence using the following parameters: RARE factor: 1, echo time (TE): 11 ms, averages: 3, matrix size (MTX): 128×128, field of view (FOV):25×25 mm2, 6 slices, slice thickness: 1.5 mm, interslice distance: 2.0 mm, repetition times, TR=15000, 10000, 8000, 6000, 3000, 1500, 1000, 750, 500, 300, 200, and 150 ms, and a total scan time of ca. 3 h 45 min. T1 values of selected regions of interest (ROIs) of 5 out of 6 slices were calculated using the T1 saturation recovery mono-exponential curve fitting formula provided by the image sequence analysis (USA) tool in Paravision 5.0.1 software (Bruker BioSpin, Billerica, Mass., USA).

Color T1 maps were generated using Jim v. 6.0 software (Xinapse Systems Ltd., Aldwincle, UK). Briefly, the desired ROIs were masked using the contour ROI function T1 maps were then generated using the saturation-recovery T1 fit function in the image-least-squares fitter entering TRs in the single input image configuration. Color maps were generated using an inverted rainbow color lookup table setting the maximum T1 to 3000 ms. Images were processed using the image resampler by resizing pixels to smooth the image by converting a 128×128 MTX to 384×384 MTX (changing the number of columns and rows under pixel resizing specifications).

T2-weighted images were acquired using a multi-slice multi-echo (MSME) pulse sequence with variable echo times using the following parameters: TR=6000 ms, averages: 3, MTX=128×128, FOV=25×25 mm2, 6 slices, slice thickness: 1.5 mm, interslice distance: 2.0 mm, TE=11, 22, 33, 44, 55, . . . 352 ms, and a total scan time of ca. 29 min. T2 values of selected regions of interest (ROIs) of 5 out of 6 slices were calculated using a T2 mono-exponential decay curve fitting formula provided by the image sequence analysis (USA) tool in Paravision 5.0.1 software (Bruker BioSpin, Billerica, Mass., USA).

Color T2 maps were generated using Jim v. 6.0 software (Xinapse Systems Ltd., Aldwincle, UK). Briefly, the desired ROIs were masked using the contour ROI function T2 maps were then generated using the single-exponential T2 decay fit function in the image-least-squares fitter entering TEs in the single input image configuration. Color maps were generated using an inverted rainbow color lookup Table setting the maximum T2 to 200 ms and the minimum T2 to 75 ms. Images were processed using the image resampler by resizing pixels to smooth the image by converting a 128×128 MTX to 384×384 MTX (changing the number of columns and rows under pixel resizing specifications).

Results:

In Vitro Labeling of Bacteria with MRI Contrast Agents

The relative affinity of Zn-1, Zn-2, and Zn-3 for bacteria was determined by quantifying the amount of GdIII bound to bacterial cells after incubation with various concentrations of each contrast agent. The binding affinity was examined for both a Gram-positive strain, S. aureus, and a Gram-negative strain, E. coli (FIG. 5).

Figure 5:
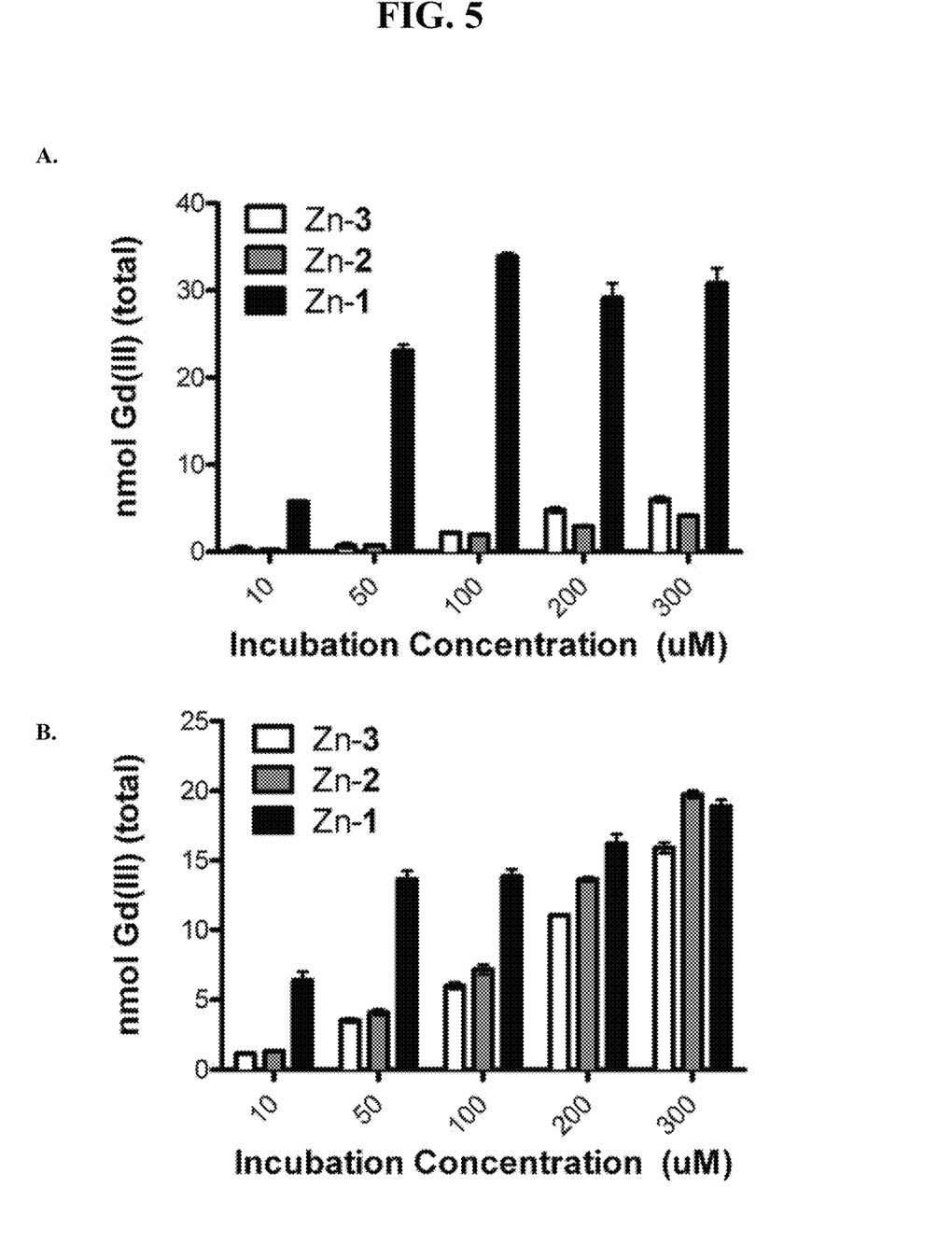

Zn-1 binds readily to S. aureus in a dose-dependent manner, with maximum binding occurring at an incubation concentration of 100 µm (FIG. 5). However, S. aureus incubated with Zn-2 and Zn-3 show only minor increases in GdIII content with increasing incubation concentrations, likely due to non-specific binding of the agents to the cell surface. At all incubation concentrations the GdIII content of Zn-2 and Zn-3 incubated S. aureus is significantly less than cells incubated with Zn-1. Specifically, the GdIII content of S. aureus incubated with 100 µm Zn-1 is approximately 16-fold higher than bacteria incubated with 100 µm Zn-2 and 18-fold higher than bacteria incubated with Zn-3 (FIG. 5).

Interestingly, Zn-2 does not show an increased affinity for the anionic bacterial membrane despite its positive charge. While the present invention is not limited to any particular mechanism, and an understanding of the mechanism is not necessary to practice the invention, this suggests that for bacteria-targeted MR contrast agents, the mechanism of interaction between the Zn-dpa groups and the membrane phospholipids requires the presence of two Zn-dpa moieties, possibly due to a cooperative-binding effect of multiple Zn-dpa moieties on the same molecule coordinating to anionic phosphates on the bacterial surface.[11e,12] Again, while the present invention is not limited to any particular mechanism, it may be that this cooperative interaction, in addition to the greater charge of the complex, is responsible for the increased affinity of Zn-1 for S. aureus.

In vitro labeling experiments with E. coli indicate that Zn-1 exhibits an affinity for Gram-negative strains; however, the extent of non-specific binding exhibited by Zn-2 and Zn-3 is much greater for E. coli than S. aureus. For lower concentrations of contrast agent (s 100 µm), Zn-1 incubated E. coli retains more GdIII than Zn-2 or Zn-3 treated cells (FIG. 5). Similar to S. aureus, the GdIII content of Zn-1 incubated E. coli increases in a concentration-dependent manner and plateaus at 50 µm (contrast agent incubation concentration) whereas the GdIII content of Zn-2 and Zn-3 incubated E. coli continues to increase even above 50 µm incubation concentrations. This supports the non-limiting hypothesis that these increases are due to non-specific binding to the surface of E. coli.

MR Imaging of Bacterial Cells Labeled with Zn-1, Zn-2, Zn-3

To evaluate the potential of Zn-1 as a molecular imaging probe, T1 and T2 relaxation times of S. aureus labeled with Zn-1, Zn-2, and Zn-3 were acquired at 1.41 T and 7 T.

Figure 6:
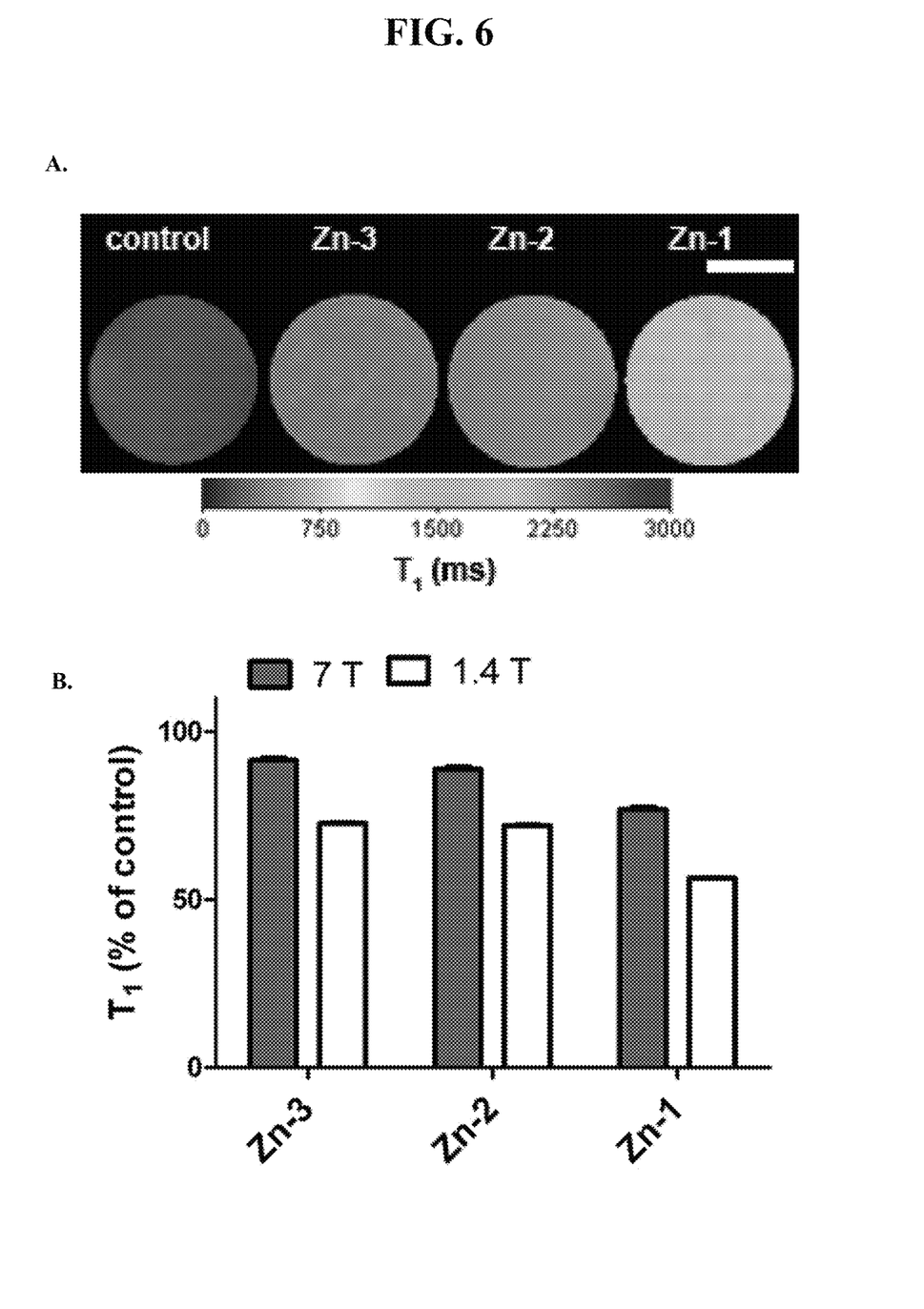

Bacteria were labeled as described above, using an incubation concentration of 300 μm contrast agent. The samples were washed with LB media and diluted in agarose to create a uniform suspension of bacteria. The T1-weighted image acquired at 7 T shows significant contrast enhancement in the Zn-1 labeled sample compared to untreated bacteria; conversely, Zn-2 and Zn-3 labeled bacteria show no such contrast enhancement (FIG. 6).

At 7 T, the T1 relaxation time of *S. aureus* cultures labeled with Zn-1 is approximately 21% lower than the T1 of untreated cultures. At 1.41 T the reduction in T1 increases to 44% (FIG. 6). Conversely, the T1 of Zn-2 and Zn-3 labeled bacteria is reduced by only 10 and 28% vs. control at 7 T and 1.41 T, respectively (FIG. 6).

The pronounced reduction in T1 relaxation observed at 1.41 T as compared to 7 T may be explained by the field strength dependence of the relationship between rotational correlation time ($\tau R$) and relaxivity.[20] Binding of MR contrast agents to large macromolecules is known to increase the $\tau R$, and subsequently the r1, of contrast agents. [20-21] While the present invention is not limited to any particular mechanism, it is believed that Zn-1 adheres to the bacterial surface, so it is reasonable to expect both the $\tau R$ and r1 of the agent to increase upon binding. However, the influence of $\tau R$ on relaxivity is dependent on the field strength; at lower field strengths (i.e. 1.41 T), the effect of TR enhancement on relaxivity is more pronounced. [20] Consequently, it is reasonable that bacteria labeled with Zn-1 exhibit greater decrease in T1 at lower field strengths.

Equation (1) used to calculate q of Zn-1-Tb. $\tau H2O$ and $\tau D2O$ are the time constants for the exponential fluorescence decay in H2O and D2O, respectively.

References (All of which are Herein Incorporated by Reference)

[1] A. Singh, R. V. Goering, S. Simjee, S. L. Foley, M. J. Zervos, Clin. Microbiol. Rev. 2006, 19, 512-530.
[2] a) W. R. Caly, E. Strauss, J. Hepatol. 1993, 18, 353-358; b) M. H. Kollef, G. Sherman, S. Ward, V. J. Fraser, Chest 1999, 115, 462-474; c) N. Rayes, D. Seehofer, T. Theruvath, A. Schiller Reinhold, M. Langrehr Jan, S. Jonas, S. Bengmark, P. Neuhaus, Am. J. Transplant. 2005, 5, 125-130.
[3] a) K. Aydinuraz, C. Agalar, F. Agalar, S. Çeken, N. Duruyürek, T. Vural, J. Surg. Res. 2009, 157, e79-e86; b) H. Chew Ben, D. Lange, Nat. Rev. Urol. 2009, 6, 440-448.
[4] B. Hirsch Elizabeth, H. Tam Vincent, Expert Rev. Pharmacoecon Outcomes Res. 2010, 10, 441-451.
[5] B. Pourakbari, S. Mamishi, J. Zafari, H. Khairkhah, M. H. Ashtiani, M. Abedini, S. Afsharpaiman, S. S. Rad, Braz. J. Infect. Dis. 2010, 14, 252-255.
[6] B. C. Pien, P. Sundaram, N. Raoof, S. F. Costa, S. Mirrett, C. W. Woods, L. B. Reller, M. P. Weinstein, Am. J. Med. 2010, 123, 819-828.
[7] L. Wang, W. Zhao, B. O'Donoghue Meghan, W. Tan, Bioconjugate Chem. 2007, 18, 297-301.
[8] S. Zhang, W. Zhang, Y. Wang, Z. Jin, X. Wang, J. Zhang, Y. Zhang, Bioconjugate Chem. 2011, 22, 369-375.
[9] C. P. J. M. Brouwer, L. Sarda-Mantel, A. Meulemans, D. Le Guludec, M. M. Welling, Mini-Rev. Med. Chem. 2008, 8, 1039-1052.
[10] X.-H. Ning, S.-J. Lee, Z.-R. Wang, D.-I. Kim, B. Stubblefield, E. Gilbert, N. Murthy, Nat. Mater. 2011, 10, 602-607.
[11] a) W. M. Leevy, S. T. Gammon, J. R. Johnson, A. J. Lampkins, H. Jiang, M. Marquez, D. Piwnica-Worms, M. A. Suckow, B. D. Smith, Bioconjugate Chem. 2008, 19, 686-692; b) K. M. DiVittorio, W. M. Leevy, E. J. O'Neil, J. R. Johnson, S. Vakulenko, J. D. Morris, K. D. Rosek, N. Serazin, S. Hilkert, S. Hurley, M. Marquez, B. D. Smith, ChemBioChem 2008, 9, 286-293; c) W. M. Leevy, J. R. Johnson, C. Lakshmi, J. Morris, M. Marquez, B. D. Smith, Chem. Commun. 2006, 1595-1597; d) W. M. Leevy, S. T. Gammon, H. Jiang, J. R. Johnson, D. J. Maxwell, E. N. Jackson, M. Marquez, D. Piwnica-Worms, B. D. Smith, J. Am. Chem. Soc. 2006, 128, 16476-16477; e) C. Lakshmi, R. G. Hanshaw, B. D. Smith, Tetrahedron 2004, 60, 11307-11315.
[12] A. J. Surman, C. S. Bonnet, M. P. Lowe, G. D. Kenny, J. D. Bell, E. Toth, R. Vilar, Chem. Eur. J. 2011, 17, 223-230, S223/221-S223/216.
[13] Y. Koga, J. Mol. Evol. 2011, 72, 274-282.
[14] F. A. Jailer, R. Weissleder, JAMA J. Am. Med. Assoc. 2005, 293, 855-862.
[15] a) P. A. Sukerkar, K. W. MacRenaris, T. J. Meade, J. E. Burdette, Mol. Pharm. 2011, 8, 1390-1400; b) P. A. Sukerkar, K. W. MacRenaris, T. R. Townsend, R. A. Ahmed, J. E. Burdette, T. J. Meade, Bioconjugate Chem. 2011, 22, 2304-2316.
[16] a) J. L. Major, R. M. Boiteau, T. J. Meade, Inorg. Chem. 2008, 47, 10788-10795; b) J. L. Major, G. Parigi, C. Luchinat, T. J. Meade, Proc. Natl. Acad. Sci. USA 2007, 104, 13881-13886.
[17] P. R. Ashton, D. W. Anderson, C. L. Brown, A. N. Shipway, J. F. Stoddart, M. S. Tolley, Chem. Eur. J. 1998, 4, 781-795.
[18] L. De Luca, G. Giacomelli, A. Porcheddu, Org. Lett. 2002, 4, 553-555.
[19] S. Quici, M. Cavazzini, G. Marzanni, G. Accorsi, N. Armaroli, B. Ventura, F. Barigelletti, Inorg. Chem. 2005, 44, 529-537.
[20] a) R. C. Strauch, D. J. Mastarone, P. A. Sukerkar, Y. Song, J. J. Ipsaro, T. J. Meade, J. Am. Chem. Soc. 2011, 133, 16346-16349; b) P. Hermann, J. Kotek, V. Kubicek, I. Lukes, Dalton Trans. 2008, 3027-3047.
[21] a) L. M. Manus, D. J. Mastarone, E. A. Waters, X.-Q. Zhang, E. A. Schultz-Sikma, K. W. MacRenaris, D. Ho, T. J. Meade, Nano Lett. 2010, 10, 484-489; b) Y. Song, X. Xu, K. W. MacRenaris, X.-Q. Zhang, C. A. Mirkin, T. J. Meade, Angew. Chem. 2009, 121, 9307; Angew. Chem. Int. Ed. 2009, 48, 9143-9147, S9143/9141-S9143/9124; c) Y. Song, E. K. Kohlmeir, T. J. Meade, J. Am. Chem. Soc. 2008, 130, 6662-6663; d) R. Cilliers, Y. Song, E. K. Kohlmeir, A. C. Larson, R. A. Omary, T. J. Meade, Magn. Reson. Med. 2008, 59, 898-902.

All publications and patents mentioned in the above specification are herein incorporated by reference. Various modifications and variations of the described compositions and methods of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the present invention.

We claim:
1. A method for imaging bacteria in a subject comprising:
a) administering a contrast agent to a subject, wherein said contrast agent is selected from the group consisting of:

Formula (I)

Formula (II)

and

Formula (III)

wherein M is a metal ion, and wherein R is a linker moiety selected from the group consisting of:
  i) an amino acid,
  ii) a peptide,
  iii) a divalent branched or unbranched carbon chain comprising from about 2 to about 30 carbon atoms,
  iv) a divalent branched or unbranched carbon chain comprising from about 2 to about 30 carbon atoms, which the chain is substituted with one or more hydroxyl groups or oxo groups,
  v) a divalent branched or unbranched carbon chain comprising from about 2 to about 30 carbon atoms, wherein one or more of the carbon atoms in the chain is replaced with an aryl ring, a hetoroaryl ring, or with a non-peroxide —O—, —S— or —NH—,
  vi) —C(=O)NH(CH$_2$)$_3$—;
  vii) —C(=O)NH(CH$_2$)$_5$C(=O)NH(CH$_2$)—;
  viii) —CH$_2$OC(=O)NH(CH$_2$)$_2$O(CH$_2$)$_2$O(CH$_2$)—, and
  ix) a divalent heteroaryl group, and
b) performing imaging of said subject and detecting a signal from said contrast agent if said subject is infected with bacteria.

2. The method of claim 1, wherein said bacteria comprises *E. coli*.

3. The method of claim 1, wherein said bacteria comprises Staphylococcus bacteria.

4. The method of claim 1, wherein said imaging comprises magnetic resonance imaging.

* * * * *